(12) United States Patent
Lu et al.

(10) Patent No.: US 6,866,856 B2
(45) Date of Patent: Mar. 15, 2005

(54) COMPOSITIONS AND DELIVERY METHODS FOR THE TREATMENT OF WRINKLES, FINE LINES AND HYPERHIDROSIS

(75) Inventors: Michelle Zheng Lu, Nanuet, NY (US); Robert E. Kalafsky, Ogdenburg, NJ (US); Michele C. Duggan, Middletown, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/334,887

(22) Filed: Dec. 31, 2002

(65) Prior Publication Data

US 2004/0127556 A1 Jul. 1, 2004

(51) Int. Cl.$^7$ .................................................. A61K 7/00
(52) U.S. Cl. ........................ 424/401; 424/65; 424/725; 424/736
(58) Field of Search .......................... 424/401, 65, 725, 424/736

(56) References Cited

U.S. PATENT DOCUMENTS

| | | | |
|---|---|---|---|
| 4,224,179 A | 9/1980 | Schneider | 252/316 |
| 4,235,871 A | 11/1980 | Papahadjopoulos et al. | 424/19 |
| 4,379,454 A | 4/1983 | Campbell et al. | 604/897 |
| 4,708,861 A | 11/1987 | Popescu et al. | 424/1.1 |
| 4,820,724 A | 4/1989 | Nimni | 514/396 |
| 4,956,171 A | 9/1990 | Chang | 424/449 |
| 5,223,262 A | 6/1993 | Kim et al. | 424/448 |
| 5,370,873 A | 12/1994 | Udeinya | 424/195.1 |
| 5,376,363 A | 12/1994 | Benfatto et al. | 424/66 |
| 5,500,209 A | 3/1996 | Ross et al. | 424/66 |
| H1541 H | 6/1996 | Holla | 424/761 |
| 5,770,222 A | 6/1998 | Unger et al. | 424/450 |
| 5,834,513 A | 11/1998 | Ptchelintsev et al. | 514/561 |
| 5,847,003 A | 12/1998 | Ptchelintsev et al. | 514/532 |
| 5,885,600 A | 3/1999 | Blum et al. | 424/405 |
| 5,932,229 A | 8/1999 | Ptchelintsev et al. | 424/401 |
| 5,998,423 A | 12/1999 | Manneth et al. | 514/260 |
| 6,069,169 A | 5/2000 | Ptchelintsev et al. | 514/532 |
| 6,153,208 A | 11/2000 | McAtee et al. | 424/402 |
| 6,239,114 B1 * | 5/2001 | Guthrie et al. | 514/32 |
| 6,251,400 B1 * | 6/2001 | Guthrie et al. | 424/736 |
| 6,338,855 B1 | 1/2002 | Albacarys et al. | 424/409 |
| 6,344,461 B1 * | 2/2002 | Breton et al. | 514/277 |
| 6,372,239 B1 | 4/2002 | Wu et al. | 424/405 |
| 6,423,327 B1 | 7/2002 | Dobson, Jr. et al. | 424/401 |
| 2002/0081291 A1 | 6/2002 | Hawrot | 424/94.63 |

OTHER PUBLICATIONS

A. Blitzer, et al., "Botulinum Toxin for the Treatment of Hyperfunctional Lines of the Face," *Arch Otolaryngol Head Neck Surg*, 119:1018–1022, Sep. 1993.

J. D. A. Carruthers and J. A. Carruthers, "Treatment of Glabellar Frown Lines with C. Botulinum–A Exotoxin," *J Dermatol Surg Oncol*, 18:17–21, 1992.

ZJ. Cui and XH. He, "The pre–synaptic blocker toosendanin does not inhibit secretion in exocrine cells," *World J. Gastroenterology*, 8(5):918–922, Oct. 15, 2002.

S. Hasegawa, et al., "Biochemistry of Citrus Limonoids and Their Anticarcinogenic Activity," *Food Phytochemicals I: Fruits and Vegetables*, pp. 198–208, 1994.

L. K. T. Lam, et al., "Inhibition of Chemically Induced Carcinogenesis by Citrus Limonoids," *Food Phytochemicals I: Fruits and Vegetables*, pp. 209–219, 1994.

L. K. T. Lam, et al., "Citrus Limonoid Reduction of Chemically Induced Tumorigenesis," *Food Technology*, pp. 104–108, Nov. 1994.

* cited by examiner

Primary Examiner—Shelley A. Dodson
Assistant Examiner—Konata M. George
(74) Attorney, Agent, or Firm—Anthony M. Santini

(57) ABSTRACT

The present invention describes compositions and methods for treating, preventing and improving the appearance of skin, particularly, treating, preventing, ameliorating, reducing and/or eliminating fine lines and/or wrinkles of skin, wherein the compositions include limonoid constituents which inhibit acetylcholine release at neuromuscular junctions of skeletal muscle so as to relax the muscles involved with wrinkling, folding and creasing of skin, e.g., facial movement and expression. The limonoids preferably include the plant alkaloids *toosendanin* and *azadirachtin*. The compositions, which also are used to treat hyperhidrosis, are preferably applied to the skin, or are delivered by directed means to a site in need thereof.

43 Claims, No Drawings

COMPOSITIONS AND DELIVERY METHODS FOR THE TREATMENT OF WRINKLES, FINE LINES AND HYPERHIDROSIS

FIELD OF THE INVENTION

The present invention generally relates to compositions and methods for skin and personal care involving components as active agents that exert their effects at the neuromuscular junction of muscle and nerve cells and tissue. Such compositions and methods are particularly suitable for the treatment and prevention of wrinkles, fine lines and hyperhidrosis of skin. More particularly, the present invention relates to compositions including plant or fruit constituents which can work at the level of the muscle and affect muscle relaxation as a consequence of the use, preferably topical use, of these compositions. Such constituents include, for example, limonoids, e.g., plant alkaloids, from the Maliaecae family, such as *toosendanin* from *Melia Toosendan* Sieb. Et. Zucc. (the Chinaberry tree) and *azadirachtin* from *Melia Azadirachta* (the Neem tree). The invention further relates to methods of delivery for such compositions so as to allow the active components to more readily reach the muscle layer and preferably function at the level of the neuromuscular junction of facial muscles, more preferably facial expression muscles, to treat, including preventing, reducing, ameliorating, and/or eliminating, signs of dermatological aging, for example, wrinkles, fine lines, folds and furrows in the skin; to treat, prevent, or reduce hyperhidrosis; and/or to improve the aesthetic appearance of the skin.

BACKGROUND OF THE INVENTION

A number of treatments and compositions for topical application are promoted in the art for mitigating dermatological conditions of the skin which frequently are associated with natural or environmental causes, such as the process of aging (i.e., intrinsic aging), exposure to the sun, or the resulting ultraviolet radiation therefrom (i.e., extrinsic aging), and the like. Other factors, such as improper care and/or diet, stress, nutritional deficiencies, repeated facial movement and genetic predisposition also contribute to the development of adverse skin conditions, such as fine lines, frown lines, folds, furrows and wrinkles.

Popular culture and trends, the fashion industry, and many arms of the current media promote and encourage a youthful appearance that reflects skin, particularly facial skin, which is free of wrinkles, fine lines and the like. In today's world, both women and men desire to maintain a youthful, wrinkle-free appearance for as long as possible and consequently seek to prevent, reduce, improve, or eliminate the signs of aging (and/or sun exposure) which reveal themselves in the forms of fine lines, furrows, and wrinkles, for example. The products commonly available to date for this purpose typically contain agents that act on the skin by merely moisturizing, promoting cell growth, swelling the extracellular matrix (by, for example, increasing or promoting the synthesis of collagen, elastin or glycosaminoglycans) which comprises skin. Calcium channel inhibitory agents that act on calcium channels of subcutaneous muscle and/or nerve tissue have also been described as components of compositions to relax and/or decontract cutaneous and/or subcutaneous tissue whose contraction is associated with wrinkle formation (U.S. Pat. No. 6,344,461 B1 to L. Breton et al.).

Compositions containing active agents and ingredients for use in personal care products to affect, prevent, and/or reduce hyperhidrosis, such as antiperspirants and deodorants, are also widely employed in the general population. Such compositions are provided to reduce and prevent perspiration and body malodor associated with human perspiration and sweating, particularly underarm malodor, and ideally should contain constituents that are effective in the treatment of sweating following topical application to the skin. While antiperspirants combat auxiliary body malodors by inhibiting perspiration through, for example, the action of astringent salts such as aluminum and zirconium salts, deodorants neutralize objectionable odors resulting from the degradation of the components of sweat which are attacked by chemicals and microbes, thereby producing foul-smelling fatty acids.

By the regular use of antiperspirants or deodorants, a considerable number of users have experienced pain and/or irritation in the sensitive skin or body surface to which the antiperspirant or deodorant is applied, due to the active salts in these compositions, as well as to skin sensitivity. As is appreciated by the practitioner, deodorants are generally less irritating to the skin than antiperspirants because deodorants do not inhibit sweat, but rather neutralize the degradation products of sweat. Despite this, however, deodorants can also be irritating to sensitive skin, particularly for those whose skin is compromised in certain areas (e.g., the underarm area) as a result of shaving. Also, deodorants are difficult to use in other sweat-prone areas (e.g., feet, palms, groin). In view of the widespread use of such personal care products, effective antiperspirant and deodorant compositions are desired to inhibit, prevent, or reduce perspiration and body malodor with less irritation to the body and skin of the user.

Many of the compositions described for various topical treatments of the skin include components, such as alpha-hydroxyacids ("AHAs"), that may provide only superficial effectiveness, or that may cause adverse side effects to the user's skin, for example, irritation. Indeed, some commonly used compositions and methods for reducing fine lines and/or wrinkles contain AHAs, such as glycolic acid, lactic acid, tartaric acid and citric acid, and salts thereof, or they contain tretinoin, also known as all-trans retinoic acid or retinol (Vitamin A), or ascorbic acid (Vitamin C), all of which, without further mitigation, can induce the above-mentioned disadvantageous effects, often due to a lowering of the pH of the skin, among other factors. To provide maximum effectiveness and to avoid or prevent the foregoing types of adverse reactions, new and alternative components of compositions and formulations for the treatment and care of the skin are desired.

Human skin comprises two major compartments: a superficial outer compartment, the epidermis, and a deeper compartment, the dermis. The outermost epidermal skin layers typically provide a certain degree of protection to the body, although fine lines and wrinkles can be readily visualized in this portion of the skin. The epidermis and dermis bear the brunt of harmful effects of photodamage. The natural human epidermis functions to provide the essential protectant role of the skin in the human body. The dermis, which provides a solid and nutritional support to the epidermis, comprises mainly fibroblasts and an extracellular matrix composed primarily of a substance that includes collagen, elastin and glycosaminoglycans ("GAGs"). In addition, the dermis contains leukocytes, mast cells, tissue macrophages, blood vessels, muscle cells and nerve fibers.

The dermal muscles of the face are controlled by motor nerve afferences of the facial nerve. The interlobular septa of the hypoderm contain within them fibers that constitute a striated muscle tissue, i.e., the panniculus carnosus. It is known that a subpopulation of dermal fibroblasts, called myofibroblasts, has contractile characteristics similar to those of muscle cells and tissue.

Botulinum toxin, (also known by the trade name, Botox®, Allergen, Irvine, Calif.), is currently in vogue for treating wrinkles and fine lines, but was initially used to treat spasms. This toxin acts on states of muscular spasticity by specifically inhibiting neurotransmission in nerve cells, thereby causing contracted muscles to relax (e.g., A. Blitzer et al., 1993, *Arch. Otolaryngol. Head Neck Surg.*, 119:118–122; U.S. Pat. No. 6,344,461 B1 to L. Breton et al.). Botulinum toxin also can act on wrinkles of the glabella (wrinkles between the eyebrows) when injected subcutaneously. (See, J. D. Carruthers, 1992,*J. Dermatol. Surg. Oncol.,* 18:17–21; U.S. Pat. No. 6,344,461 B1 to L. Breton et al.). However, the full extent of adverse effects related to long-term use of botulinum toxin and products or treatments containing this material are still not well established. Botulinum toxin treatment has been associated with a number of side effects including, transient fatigue, dysphagia, neck weakness, hoarseness, and localized pain. In addition, many patients who preliminarily respond to botulinum toxin subsequently become non-responsive to treatment. (See, e.g., published U.S. Patent Application No. US2002/00812914 to Hawrot).

New ingredients for use as effective, active agents in compositions and formulations for application, preferably topical application, to the skin are advantageous to the industry and the consumer for a variety of uses in the areas of skin care treatment and therapy, and personal use products.

Plant extracts and substances serving a variety of diverse purposes include limonoid constituents of the Maliaecae and Rutaceae families. Limonoids are a group of chemically related triterpene derivatives which are among the bitter principles found in citrus fruits such as lemons, lime, orange and grapefruit. They are also present as glucose derivatives in mature fruit tissues and seeds, and are one of the major secondary metabolites present in citrus. More specific examples of such plant materials include the plant alkaloids *toosendan* (from *Melia Toosendan* Sieb. Et. Zucc), (i.e., Chinaberry) and *azadirachtin* (from *Melia Azadirachta* (i.e., Neem). Limonoids have been known to have insecticidal properties (e.g., U.S. Pat. No. 6,372,239 to Wu et al.; U.S. Pat. No. 5,885,600 to M. Blum et al.), as well as anti-neoplastic and anti-carcinogenic effects in laboratory animals (e.g., U.S. Pat. No. 5,370,873 to I. J. Udeinya; U.S. Pat. Nos. 6,239,114 and 6,251,400 to N. Guthrie et al.). The furan moiety attached to the D-ring is specifically responsible for detoxifying the chemical carcinogen glutathione-S-transferase enzyme system (Lam et al., 1994, *Food Technology,* 48:104–108).

Citrus fruit tissues and the byproducts of juice processing, such as peels and molasses are sources of limonoid glucosides and citrus seeds contain high concentrations of both limonoid aglycones and glucosides. Limonoid aglycones in the fruit tissues gradually disappear during the late stages of fruit growth and maturation. Thirty-eight limonoid aglycones have been isolated from citrus. The limonoids are present in three different forms, namely, the dilactone is present as the open D-ring form (monolactone), the limonoate A-ring lactone and the glucoside form (See, e.g., U.S. Pat. No. 6,239,114 to N. Guthrie et al.). Only the monolactones and glucosides are present in fruit tissues. (Hasegawa S. et al., 1994, In: Food Phytochemicals for Cancer Prevention I, Eds M-T. Huang et al, American Chemical Society, 198–207).

Procedures for the extraction and isolation of both aglycones and glucosides have been established to obtain concentrated sources of various limonoids (Lam, L. K. T. et al., 1994, In: Food Phytochemicals for Cancer Prevention, Eds. M. Huang, T. Osawa, C. Ho and R. T. Rosen, ACS Symposium Series 546, p 209).

Safe, effective and new components of compositions to treat, prevent, reduce, inhibit, and/or improve the dermatological signs of aging, as well as hyperhidrosis, would be advantageous for the formulation of treatments and products for the skin. As described herein, novel and beneficial methods and compositions, as well as their mode of action, for the treatment of wrinkles and the like, as well as for personal care products for the skin, are provided by the present invention.

SUMMARY OF THE INVENTION

The present invention provides compositions and methods comprising plant-derived constituents newly found to be effective to treat, including prevent, reduce, ameliorate, and/or eliminate, signs and results of dermatological aging of skin, especially wrinkles and fine lines, and/or to improve the aesthetic appearance of skin. Further these constituents are provided for use in compositions and methods to treat, including prevent, ameliorate, and/or reduce, hyperhidrosis (or sweating or perspiration) and its associated effects, such as malodor. More specifically, the active constituents (also referred to as active agents, components, ingredients, reagents, or compounds herein) are limonoids, obtained from plants and the like, of the Maliaecae family. Nonlimiting examples of limonoids for use in accordance with this invention include the plant alkaloids *toosendanin* from *Melia Toosendan* Sieb. Et. Zucc (more commonly known as the Chinaberry tree, Ku Lian Pi extract, or *Melia azedarach*); and *azadirachtin* from *Melia Azadirachta* (more commonly known as the Neem tree or *Azacdiracta indica*). These plant materials have been newly found to provide treatment for wrinkles, fine lines and other signs of dermatological aging (i.e., intrinsic aging) or sunlight exposure of the skin (i.e., extrinsic aging), as well for use in the treatment of hyperhidrosis, by virtue of their effect at the neuromuscular junction (NMJ) of muscle and nerve cells and tissue, and at the fibers of the sweat glands to inhibit acetylcholine release, e.g., at the NMJ, thereby relaxing or decontracting muscles, e.g., facial expression muscles.

It is to be understood that, as used herein, the terms treating and treatment include and encompass preventing, reducing, ameliorating, improving, alleviating, and/or eliminating the dermatological effects of aging and sun exposure, with particular regard to wrinkles, fine lines, folds, furrows, creases of the skin, and the like. The present invention further encompasses the treatment, as defined above, of "marionette" lines that run on either side of the mouth, as well as lines on the forehead, and the perpendicular lines between the brows. The present compositions and methods are also suitable for use in treating, as defined above, dermatological conditions of the skin in numerous areas of the body, including, without limitation, the face, forehead, neck, arms, hands, legs, knees, feet, chest, back, groin, buttocks, and the like.

It is another aspect of the present invention to provide compositions, formulations and methods containing materials newly determined to be useful in the treatment of wrinkles, fine lines, folds, furrows and other signs of aging skin, in addition to treating, preventing or reducing hyperhidrosis. These materials exert their effectiveness according to this invention by preferably working at the neuromuscular junctions (NMJ), such as in the muscle and nerve cell or tissue layer of a site of application, e.g., skin of the face, neck, arms, feet, or hands, or in the dermal layer of the skin where sweat glands are located. More specifically, the limonoid constituents (i.e., chemical actives, such as *toosendanin* or *azadirachtin*, or a combination thereof) block or inhibit the release of acetylcholine at the NMJ of skeletal muscle, which, in turn, results in the relaxation or decontraction of contracted muscles. Contracted muscles are associated with the formation of fine lines, wrinkling and the like.

According to the present invention the materials, in general, comprise plant alkaloids, or limonoids of the Maliaecae family. More specifically, the limonoids comprise *toosendanin* and *azadirachtin*, which were not previously known to inhibit acetylcholine release in NMJ of skeletal muscles, thereby relaxing the facial expression muscles, for example, to treat, prevent, reduce, ameliorate, and/or eliminate aesthetically displeasing wrinkles, frown lines, fine lines, folds, furrows, or neck bands, etc. that can arise from aging, prolonged sun exposure of the skin, ultraviolet radiation associated with sun or photoexposure, or in particular, hyperactive facial expression muscles.

In addition, because it is understood that the contraction or hypercontraction of certain muscles, particularly facial muscles, is related to the appearance of wrinkles, fine lines, etc., the relaxation of such muscles, and/or the control or modulation of the contraction of such muscles, by the newly-determined action of the limonoids as disclosed herein can serve a pivotal function in the treatment, prevention, reduction, amelioration, or elimination of wrinkles, fine lines and the like.

In accordance with this invention the limonoid materials comprise compositions which include, without limitation, topically applied sunscreens, anti-oxidants, anti-inflammatories, cosmetics, including makeups, anti-aging formulations, e.g, creams for fine lines and/or wrinkles, topicals, skin permeants antiperspirants, deodorants and the like. Also in accordance with this invention, ingredients, components, or compounds that are formulated in such compositions in a variety of product forms, e.g., transdermals, such as patches, and the like, are encompassed, particularly for topical administration.

Another aspect of the present invention provides the compositions comprising the limonoid materials preferably for topical administration without inducing significant irritation. Further, such compositions are preferably delivered by, but not limited to, the use of targeted delivery systems, for example, liposomes, microspheres, transdermal patches, and the like, so that the actives can more readily reach and affect the muscle layer of the area of application, e.g., face or neck, or the dermal layer of the skin, where sweat glands are located, e.g., underarm, foot, hand, etc. Compositions comprising limonoid constituents, including liposome formulations, can be administered by direct injection subcutaneously, intradermally, or through iontophoresis, to deposit the active agents at the sites requiring muscle relaxation or decontraction.

In another of its aspects, the present invention provides limonoid-containing compositions and methods thereof which can improve the aesthetic appearance of the skin by treating, including preventing, ameliorating and/or reducing at least one of the following: dermatological aging, especially chronological, actinic or hormonal aging. The improvement preferably results following topical application of a product or formulation containing one or more of the limonoid constituents as described herein.

Another aspect of this invention provides a method of reducing, preventing, treating, or ameliorating wrinkles, fine lines, creases, frown lines, or other signs of dermatological aging, or photoexposure of skin, comprising: applying a composition comprising an acetylcholine antagonist at a site comprising a neuromuscular junction (NMJ) in an amount effective to reduce or block acetylcholine release at the neuromuscular junction (NMJ), wherein the reduction or block of acetylcholine release at the neuromuscular junction (NMJ) concomitantly reduces or blocks muscle cell or tissue contraction (or contractility), thereby treating, preventing, reducing, ameliorating, or eliminating the formation of wrinkles, fine lines, creases, folds, frown lines, or other signs of dermatological aging, hyperactive facial expression muscles, or photoexposure. Preferably, the acetylcholine antagonist is a limonoid constituent, more preferably a limonoid constituent of the Maliaecae family, and most preferably, *toosendanin* or *azadirachtin*.

A further aspect of this invention provides a method of reducing, preventing, treating, or ameliorating hyperhidrosis or perspiration, particularly, excessive perspiration, comprising: applying a composition comprising an acetylcholine antagonist at a site comprising a neuromuscular junction (NMJ), preferably in the fibers of a sweat gland, in an amount effective to reduce or block acetylcholine release at the neuromuscular junction (NMJ), wherein the reduction or block of acetylcholine release at the neuromuscular junction (NMJ) concomitantly reduces or blocks contraction (or contractility) of cells in the dermis associated with the sweat gland, thereby reducing, preventing, treating, or ameliorating hyperhidrosis or perspiration. Preferably, the acetylcholine antagonist is a limonoid constituent, more preferably a limonoid constituent of the Maliaecae family, and most preferably, the limonoids *toosendanin* or *azadirachtin*.

Further aspects, features and advantages of the present invention will be better appreciated upon a reading of the detailed description of the invention.

DESCRIPTION OF THE INVENTION

The present invention provides novel compositions and methods comprising components newly found to be effective to treat, including prevent, reduce, ameliorate, inhibit, alleviate, and/or eliminate signs and results relating to the dermatological aging of skin due to chronological and/or hormonal aging, or due or to photoexposure (e.g., to the sun, or ultraviolet radiation) of skin, especially wrinkles, creases, furrows, folds and fine lines; and/or to improve the aesthetic appearance of skin. These components are further provided for use in compositions and methods to treat, including prevent, ameliorate, inhibit and/or reduce, hyperhidrosis (sweating or perspiration) and its associated effects, such as malodor and unaesthetic appearance.

More specifically, the components (also referred to as active agents, constituents, ingredients, reagents, substances, or compounds herein) of this invention are limonoids, obtained from plants and the like, preferably of the Maliaecae family. Nonlimiting examples of limonoids for use in accordance with this invention include the plant alkaloids *toosendanin* from *Melia Toosendan* Sieb. Et. Zucc (more commonly known as the Chinaberry tree or *Melia azedarach*); and *azadirachtin* from *Melia Azadirachta* (more commonly known as the Neem tree or *Azacdiracta indica*). *Azadirachtin* is a limonoid of the tetranortriterpenoid type. These plant materials have been newly determined to be effective constituents in compositions and methods for treating, preventing, reducing, inhibiting, improving and/or eliminating wrinkles, fine lines, creases, folds, furrows, and other signs of dermatological aging due to chronological and/or hormonal aging, or due to sunlight exposure of the skin, as well for use in the treatment of hyperhidrosis.

According to the present invention, yet without wishing to be bound by theory, the limonoid constituents exert their effects by their ability to inhibit, block, reduce, or prevent the release of acetylcholine at the neuromuscular junction (NMJ) of skeletal muscle cells and tissue, thereby relaxing muscles, for example, muscles associated with facial movement or expressions, or the fibers of the sweat glands. Both nerve and muscle cells (skeletal muscle cells) are electrically excitable and the junctions between these types of cells are known as NMJ. It has been known for many years that the stimulation of a motor nerve innervating a skeletal muscle also causes the release of acetylcholine and that acetylcholine, in turn, stimulates the skeletal muscle to contract. Thus, acetylcholine has been identified as the neurotransmitter at the neuromuscular junction. (see, e.g., B. Alberts et al., 1989, *Molecular Biology of the Cell*, $2^{nd}$ Ed., Chapter 19, The Nervous System, Garland Publishing, Inc., NY., pp. 1075 et seq.). Provided by the present invention are limonoid constituents which are newly described herein to inhibit, reduce, block, or prevent the release of acetylcholine at the NMJ of the skeletal muscle and thus relax the muscles, preferably those associated with facial expression or movement, particularly when employed in the compositions and methods of the invention. By also being able to inhibit acetylcholine release in the fibers of the sweat glands, compositions and methods comprising the limonoid constituents as described herein can reduce, treat, and/or prevent excessive sweating or perspiration.

The ability of the limonoid constituents to inhibit acetylcholine release by muscle cells results in a modulation of motor contraction so as to relax the muscle fibers in cutaneous or subcutaneous muscle and/or nerve tissue, thereby attenuating wrinkles, as well as fine lines, folds, furrows, and the like. By relaxing or preventing the contraction or hypercontraction of the cutaneous or subcutaneous muscle cells of areas such as the face, or hands, feet, etc., the limonoids and compositions containing limonoids can effectively smooth out the landscape of the skin in those areas where muscle contraction is involved in the formation of wrinkles and the like. Thus, if muscle cell contractility is associated with the formation of wrinkles, fine lines, etc., the relaxation or decontraction of the contractility of cutaneous or subcutaneous muscle tissue by the limonoid actives in the compositions of this invention can serve to loosen or slacken the contracting muscle tissue and alleviate, reduce, ameliorate, inhibit, or eradicate the wrinkles, fine lines, etc. Contraction of cutaneous or subcutaneous muscle cells or tissue of skin can elicit wrinkling, fine lines, and the like, which constitute at least some of the visible dermatological effects of aging due to chronological and/or hormonal aging, and/or due to photoexposure, as described herein.

Thus, in one of its embodiments, the present invention encompasses compositions, formulations and methods containing components, preferably, limonoid constituents, newly determined to be useful in the treatment of wrinkles, fine lines, folds, furrows and other signs of aging and/or photoexposure of skin, in addition to treating, preventing or reducing hyperhidrosis. Skin in a variety of areas of the body is amenable for treatment and/or receipt of the compositions of the present invention, including the face, forehead, neck, arms, legs, hands, feet, torso (chest), back, and the like.

The plant-derived materials exert their effectiveness according to this invention by preferably working at the neuromuscular junctions (NMJ), such as in and around muscle and nerve cells and tissue at a site of application, e.g., the skin of face, neck, arms, feet, hands, or chest, or in the dermis layer of the skin where sweat glands are located. According to this invention, the materials, in general, comprise limonoids, which are plant alkaloids, of the Maliaecae family. More specifically, the limonoids comprise *toosendanin* and *azadirachtin*, which are plant alkaloids. Prior to the present invention, these materials were not previously known or recognized to inhibit acetylcholine release at NMJ of skeletal muscles, thereby relaxing muscles associated with aesthetically displeasing wrinkles, frown lines, fine lines, folds, furrows, creases, neck bands, and the like, that can arise from aging due to chronological and/or hormonal aging, prolonged or overexposure of the skin to the sun, ultraviolet radiation associated with photoexposure, or overexercised expression muscles.

In general, for the purposes of the present invention, a substance, such as a limonoid constituent of the described compositions, is recognized as being a muscle relaxant when it elicits a relaxation effect on contracted muscle cells or on tissue, such as cutaneous or subcutaneous muscle tissue, and/or exhibits an inhibitory effect on acetylcholine release at the NMJ. Contracted muscle cells or tissue is associated with formation of wrinkles, fine lines, etc. Relaxation or decontraction of contracted muscle, such as by the action of limonoids to inhibit or block acetylcholine release at the NMJ, serves to smooth out the landscape, or microrelief, of the skin, thereby effecting the prevention, amelioration, reduction, and/or eradication of wrinkling and fine line, etc. formation caused by contracted muscle tissue in skin.

For use in the compositions of this invention, the limonoid plant alkaloids can be chemically synthesized. Alternatively, these plant alkaloids may be extracted from plants. When extracted, they may be in a pure form, a semi-purified form, or may be a component of an unpurified plant extract. For example, *toosendanin* may be extracted from the plants *Melia toosendan* Sieb. et Zucc. and *Melia azedarach* L. *Azadirachtin* may be extracted from the plant *Melia azedarach* L. As a result of some structural similarity, *azadirachtin* may mimic the function of *toosendanin*. Further, the compositions of the present invention can comprise a combination of plant alkaloids that are formulated to achieve the desired effects to combat wrinkles, and the like, and hyperhidrosis. The alkaloids as active ingredients may exert their effects via multiple mechanisms and signal transduction pathways.

The limonoid plant alkaloids contained in the compositions of the present invention can be chemically synthesized at industrial scale in large amounts. Alternatively, the alkaloids may be extracted from natural raw materials from plants. Any and all methods of preparation may be used, including the use of cultured plant seed cells, as disclosed in commonly owned patent application U.S. Ser. No. 10/040, 242, which is hereby incorporated by reference herein. The level of extraction and the degree of purity of the alkaloid may vary. For example, unpurified plant extracts may be employed in the present invention. Depending on the solubility of the particular plant alkaloid in water or in organic solvent, the extraction process for each alkaloid may differ. Two methods for extracting the alkaloids from raw plant materials include organic solvent extraction, and aqueous-organic solvent extraction, as described in U.S. Pat. No. 6,372,239 to Wu et al. The organic extraction method involves a step of continuous washing and extracting the plant material against a stream of organic solvent. Examples of organic solvents include, but are not limited to methanol, ethanol, dichloromethane, chloroform, xylene, and petroleum ether. Alternatively, the alkaloid can be partially purified or completely purified. Chemical synthesis of the alkaloid obviates the need for extraction and purification.

In accordance with this invention, the limonoid constituents comprise compositions which include, without limitation, topically applied formulations, anti-oxidants, anti-inflammatories, sunscreens, cosmetics, including make-ups, anti-aging formulations, e.g., creams for fine lines and/or wrinkles, topicals, skin penetration enhancers, antiperspirants, deodorants, and the like. Also in accordance with this invention, the limonoid constituents and additional ingredients comprising such compositions can be formulated in a variety of product forms. Preferably, the compositions are prepared in targeted delivery systems, e.g., transdermals, such as patches, and the like, particularly for topical administration.

The present invention encompasses compositions comprising one or more limonoid constituents, preferably in a pharmaceutically-acceptable cosmetic or dermatological formulation which is suitable for contact with living animal tissue, including human tissue, and for topical administration, with virtually no adverse physiological effect, e.g., irritation, to the user. Thus, the inventive compositions are especially suitable for sensitive skin.

Compositions embraced by this invention can be provided in any cosmetically and/or dermatologically suitable form, preferably as a lotion, gel, cream, or incorporated into a transdermal patch, and also in an ointment or oil base, as well as in a sprayable liquid form. Other suitable cosmetic product forms for the compositions of this invention include, for example, an emulsion, a mousse, a lip balm, a lip gloss, a lotion, a mask, an ointment, a pomade, a solution, a serum, a spray, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, and the like, as well as other botanicals such as aloe, chamomile, and the like, and as further described below. The compositions are preferably applied topically once or twice daily. The daily application can be for periods of up to two weeks, four weeks, or more.

In one embodiment encompassing sunscreen formulations, the compositions comprising limonoid constituents can further include, without limitation, ingredients such as avobenzone, cinnamic acid derivatives (e.g., octylmethoxycinnamate), octyl salicylate, oxybenzone, titanium oxide, zinc oxide and mixtures or combinations thereof. Such formulations can also preferably include an alpha hydroxy acid, an oxa acid, an oxa diacid, and mixtures or combinations thereof.

The compositions of this invention can also be formulated into liposomes which can comprise other additives or substances, and/or which can be modified to more specifically reach or remain at a site following administration. Alternatively, the limonoid-containing compositions can be injected subcutaneously (s.c.) or intradermally (i.d.) at a site in need of wrinkle, fine line, etc. reduction, improvement, prevention, and/or elimination, resulting from inhibition of acetylcholine release at the NMJ and concomitant relaxation of contracted muscle.

Pharmaceutical or physiologically acceptable compositions suitable for use in the present invention include compositions in which the active constituents, ingredients, or materials are contained in an amount effective to achieve the intended purpose. By way of example, in the present compositions, a limonoid constituent is present in an amount of from about 0.0001 wt % to about 10 wt %, based on the total weight of the composition. More preferably, the present compositions include one or more limonoid constituents in an amount from about 0.0005 wt % to about 5 wt %. Most preferably, the present compositions include one or more limonoid constituents in an amount from about 0.001 wt % to about 1 wt % of the total composition.

The determination of an effective dose or amount is well within the capability of those skilled in the art. A therapeutically effective dose refers to that amount of active ingredient, for example, a limonoid constituent identified in accordance with the present invention, which, for instance, treats, prevents, ameliorates, reduces, or eliminates the condition, more specifically, wrinkles, fine lines, creases, and the like. The practitioner, who will consider the factors related to the individual requiring treatment, will determine the exact dosage. Dosage and administration are adjusted to provide sufficient levels of the active constituent or to maintain the desired effect. Factors which are typically considered include the severity of the individual's particular need, general health of the patient, age, weight, and gender of the individual, diet, time and frequency of administration, drug combination(s), reaction sensitivities, and tolerance/response to treatment. As a general guide, long-acting pharmaceutical compositions can be administered once daily, every 2 to 4 days, every week, or once every two weeks, depending on half-life and clearance rate of the particular formulation. Variations in these dosage levels can be adjusted using standard empirical routines for optimization, as is well understood in the art. Guidance as to particular dosages and methods of delivery is provided in the literature and is generally available to practitioners in the art. Those skilled in the art will employ different formulations depending upon the nature, e.g., structure, composition, of the active limonoid constituent.

With particular regard to limonoids as anti-hyperhidrosis agents in antiperspirant or deodorant compositions and formulations for personal use, such products embrace a wide variety of dosage forms, such as sticks, gels, roll-ons, aerosols, and creams. These dosage forms generally contain a solution of the active ingredient in a solvent, usually non-aqueous, or in a multiphasic dispersion or emulsion in which a solution of the active ingredient is dispersed in some continuous phase or in which the solubilized active ingredient constitutes the continuous phase. To produce natural-looking products that leave minimal visible residue on the skin, clear and translucent antiperspirants, e.g., sticks or gels, can be utilized. Clear or translucent gelled antiperspirant sticks which are substantially anhydrous, typically contain the active material, a stabilizer as an essential component, and are gelled in a gelling agent, such as dibenzylidene monosorbitol acetal (see, e.g., U.S. Pat. No. 5,376,363 to A. J. Benfatto et al.). Other compositions provide antiperspirant active materials in gellants of different types, such as polyamide gelling agent (e.g., U.S. Pat. No. 5,500,209 to M. S. Mendolia et al.).

The compositions of the present invention yield improvements to the aesthetic appearance of the skin by treating at least one of the following: signs of dermatological aging, especially chronological, actinic or hormonal aging, or signs of extrinsic aging, such as sun exposure. In particular, improvements to the aesthetic appearance of skin include at least one of the following: makes facial lines appear less noticeable, makes facial lines and/or wrinkles feel plumped, improves appearance of suborbital lines and/or periorbital lines, improves appearance of crow's feet, reduces and/or diminishes the appearance of wrinkles, particularly facial wrinkles on the cheeks, forehead (e.g., perpendicular wrinkles between eyes, horizontal wrinkles above the eyes), and/or around the mouth, (e.g., marionette lines), and particularly deep wrinkles, folds, or creases, improves skin suppleness, reduces and/or eliminates fine and/or deep lines, folds and creases, and smoothes skin, e.g., to the extent that it reduces wrinkling/lines.

Embraced by the present invention are transdermal modes of delivery, such as patches and the like, with or without a suitable skin penetration enhancer. The methods and compositions embodied by the invention provide a means by which the one or more limonoid constituents can be effectively administered in a transdermal system. Frequently, compounds having poor topical absorption, or which are required at high dosage levels, are delivered transdermally. Accordingly, a transdermal means of delivering a composition or formulation (often with a skin penetration enhancer composition) to the skin is that of the transdermal patch or a similar device as known and described in the art. Examples of such devices are disclosed in U.S. Pat. Nos. 5,146,846, 5,223,262, 4,820,724, 4,379,454 and 4,956,171; such descriptions are not meant to be limiting. The transdermal mode of storing and delivering the compositions onto the skin and forming the active composition is convenient and well suited for the purposes of an embodiment of the present invention. Preferably, when a topical patch is used, the patch is applied to the desired area for extended period of time. Preferably, the extended period of time is greater than one hour; more preferably, the extended period of time is overnight, e.g., when the user is sleeping.

A particular embodiment of the present invention is directed to the delivery of the described compositions by the use of targeted delivery systems, for example, liposomes, microspheres (see, e.g., U.S. Pat. No. 5,770,222 to Unger et al.), transdermal patches, and the like, so that the limonoid actives can more readily reach and affect the muscle layer of the area of application, e.g., face or neck, or the dermis layer of the skin, where sweat glands are located, e.g., underarm, foot, hand, etc. Compositions comprising limonoid constituents, including liposome formulations, can also be administered by direct injection subcutaneously or intradermally to more precisely deposit the active agents at sites which require muscle relaxation or decontraction via acetylcholine release inhibition.

Liposomes and delivery systems and vehicles involving liposomes are well-known in the art. In brief, liposomes are unilamellar or multilamellar lipid vesicles which entrap a significant fraction of aqueous solution. The vesicular microreservoirs of liposomes can contain a variety of water-soluble materials, which are suspended within the emulsion (e.g., reviewed in G. Gregorius (Ed.), 1991, *Liposome Technology*, Vols. I, II, III, CRC Press, Boca Raton, Fla.; Davis S. S. and Walker I. M., 1987, *Methods in Enzymology*, 149:51–64; Mayhew E. et al., 1987, *Methods in Enzymology*, 149:64–77; and Shafer-Korting M. et al., 1989, *J. Am. Acad. Dermatol.*, 21:1271–1275). The preparation of liposomes and the variety of uses of liposomes in biological systems have been described (e.g., in U.S. Pat. No. 4,708,861 to M. C. Popescu et al., U.S. Pat. No. 4,224,179 to M. Schneider and U.S. Pat. No. 4,235,871 to D. P. Papahadjopoulos et al.). Accordingly, such liposomes can be formulated into any of the dermatological or cosmetic compositions as described herein.

In addition to the limonoid constituents as active agents, as described herein, the physiologically acceptable and pharmaceutical compositions can contain suitable pharmaceutically acceptable carriers, diluents, or excipients comprising auxiliaries which facilitate processing of the active compounds into preparations which can be used pharmaceutically. Further details on techniques for formulation and administration are provided in the latest edition of *Remington's Pharmaceutical Sciences* (Mack Publishing Co.; Easton, Pa.). Pharmaceutical compositions containing the limonoid ingredients of the present invention can be manufactured in a manner that is known in the art, e.g., by means of conventional mixing, dissolving, granulating, dragee-making, levigating, emulsifying, encapsulating, entrapping, or lyophilizing processes.

If applicable, the pharmaceutical composition can be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preparation can be a lyophilized powder.

A preferred embodiment of the topical compositions of the present invention also includes at least one of the following: a surface smoother, a skin plumper, an optical diffuser, a sunscreen, an exfoliation promoter, or an antioxidant.

A surface smoother provides the functional benefits of enhancing skin smoothness and reducing the appearance of fine lines and coarse wrinkles. Examples include, without limitation, isopropyl myristate, petrolatum, isopropyl lanolate, silicones (e.g., methicone, dimethicone), or any mixtures thereof. The surface smoother is preferably present from about 0.1 wt % to about 50 wt % of the total weight of the composition. A skin plumper serves as a collagen enhancer to the skin. An example of a suitable and preferred skin plumper is palmitoyl oligopeptide. Other nonlimiting examples of skin plumpers include collagen and/or glycosaminoglycan (GAG) enhancing agents. The skin plumper is preferably present from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 wt % to about 20 wt % of the total weight of the composition.

In another embodiment, the present invention embraces a sunscreen that protects skin from damaging ultraviolet rays. Illustratively, the sunscreen provides both UVA and UVB protection by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixture or combination thereof. Preferably, the sunscreen is present from about 1 wt % to about 30 wt % of the total weight of the composition. In particular, the addition of a sunscreen is preferred to prevent/reduce the photodegradation of the composition and/or ingredients therein while in the package and/or on the skin after application.

It will be appreciated that the compositions of the present invention containing sunscreen bring about additional improvements to the aesthetic appearance of skin, including at least one of the following: minimizes sunburning, minimizes tanning, reduces redness, and reduces future wrinkle development. It will be appreciated that when the topical composition is intended to be applied prior to retiring for the evening, the addition of a sunscreen agent may not be preferred.

The present compositions may also have one or more exfoliation promoters. Suitable examples of an exfoliation promoter that can be used in the present compositions include keratolytic agents, i.e., an active agent having desquamating, exfoliant, or scrubbing properties, or an active agent which can soften the horny layer of the skin; alpha (α) and/or beta (β) hydroxy acids; benzoyl peroxide; keto acids, such as pyruvic acid, 2-oxopropanoic acid, 2-oxobutanoic acid, and 2-oxopentanoic acid; oxa acids, as disclosed in U.S. Pat. Nos. 5,847,003 and 5,834,513, the disclosures of which are incorporated herein by reference; urea; retinoids, or any mixtures thereof. These anti-wrinkle or anti-fine line active agents can be formulated, for example, in amounts of from about 0.0001% to 5% by weight relative to the total weight of the composition.

More specifically, examples of hydroxy acids include, but are not limited to, α-hydroxy acids or β-hydroxy acids, either linear, branched, cyclic, saturated or unsaturated. The hydrogen atoms in the carbon-based backbone of these materials can be substituted with halogens, halogen-containing alkyl, acyl, acyloxy, alkoxycarbonyl, or alkoxy radicals having from 2 to 18 carbon atoms. Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof. Preferred exfoliation promoters are 3,6,9-trioxaundecanedioic acid, glycolic acid, lactic acid, or any mixtures thereof. Other acids, such as oxa acid (e.g., U.S. Pat. No. 6,069,169) and an oxa diacid (e.g., U.S. Pat. No. 5,932,229) can be included in the compositions of this invention.

When the present invention includes an exfoliation promoter, the composition typically includes about 0.5 wt % to 30 wt %, preferably about 1 wt % to about 15 wt %, more preferably about 2 wt % to about 10 wt %, and most preferably about 4 wt %, of the exfoliation promoter based on the total weight of the composition.

An antioxidant functions, among other things, to scavenge free radicals from skin to protect the skin from environmental agressors. Examples of antioxidants that can be used in the present compositions include compounds having phenolic hydroxy functions, such as ascorbic acid and its derivatives/esters; beta-carotene; catechins; curcumin; ferulic acid derivatives (e.g., ethyl ferulate or sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those having one or more thiol (—SH) functions, in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention can include an antioxidant preferably from about 0.001 wt % to about 10 wt %, and more preferably from about 0.001 wt % to about 5 wt %, of the total weight of the composition.

The compositions of this invention can also include one or more of the following ingredients, additives, or adjuvants: anesthetics, anti-allergenics, anti-fungals, antiseptics, chelating agents, colorants, dyestuffs, demulcents, emollients, emulsifiers, fragrances, fillers, humectants, lubricants, moisturizers, pH adjusters, pigment altering agents, preservatives, skin penetration enhancers, stabilizers, surfactants, thickeners, viscosity modifiers, hydrophilic or lipophilic gelling agents, vitamins, or any mixtures thereof. The amounts of these various ingredients, additives, adjuvants, or active agents are those that are conventionally used in the cosmetic or pharmaceutical fields, for example, they can constitute from about 0.01% to 20% of the total weight of the composition. In addition, the adjuvants, ingredients, additives, or active agents can be introduced into the fatty phase, into the liquid phase, and/or into lipid vesicles, depending on their nature.

The component(s) of the present invention are preferably contained in a cosmetically acceptable medium (i.e., vehicle, diluent or carrier). In an embodiment embracing topical application, the compositions of this invention comprise a medium that is compatible with human skin. The compositions can be formulated as aqueous, alcohol, or aqueous/alcohol-based solutions, ointments, lotions, gels, water-in-oil, oil-in-water, or water-oil-water triple emulsions having the appearance of a cream or gel, microemulsions, or aerosols. In addition, the compositions can be in the form of vesicular dispersions containing ionic and/or nonionic lipids, as described above. Dosage units suitable for such pharmaceutical compositions are formulated according to the conventional knowledge and techniques used in the art.

More particularly, the compositions for topical application can be in the form of a protective care composition for the skin, preferably for the face, the neck, the hands, the feet, or other areas of the body. Nonlimiting examples include day creams or lotions, night creams or lotions, sunscreen creams, lotions, or oils, body milks, makeup (a foundation), artificial tanning compositions and depilatories.

If the composition of the invention is an emulsion, the proportion of fatty substances comprised therein can range from about 5% to 80%, by weight, preferably from about 5% to 50% by weight, relative to the total weight of the composition. The fatty substances and emulsifiers used in the composition in emulsion form are one or more of those conventionally employed in the cosmetic or pharmaceutical field. Nonlimiting examples of fatty substances include mineral oils (e.g., petroleum jelly), plant oils and hydrogenated derivatives thereof, animal oils, synthetic oils (e.g., perhydrosqualene), silicone oils (e.g., polydimethylsiloxane) and fluoro oils. Other exemplary fatty substances include fatty alcohols (e.g., stearyl or cetyl alcohol), fatty acids (e.g., stearic acid) and waxes.

Emulsifiers are typically present in the compositions of the invention in an amount of about 0.3% to 30%, by weight and preferably from about 0.5% to 30% by weight relative to the total weight of the composition.

In one embodiment, the present invention relates to the administration of an effective amount of at least one limonoid constituent or composition comprised thereof to inhibit or block acetylcholine release by nerve cells at the NMJ to relax and/or decontract subcutaneous muscles, particularly facial expression muscles, thereby smoothing out or unwrinkling skin, wherein the inhibition of acetylcholine release by nerve cells at the NMJ corresponds to muscle, preferably facial expression muscle relaxation or decontraction.

In another embodiment, the present invention encompasses a method of treating fine lines, wrinkles, and/or other dermatological effects of aging or photoexposure of skin, comprising applying to skin a composition containing a limonoid in a cosmetically and/or dermatologically acceptable medium, and in an amount effective to treat, reduce, prevent and/or ameliorate fine lines, wrinkles and/or other dermatological effects of aging of skin. In the method the limonoid is preferably a member of the family Maliaecae, more preferably the limonoid is a plant alkaloid, most preferably *toosendanin, azadirachtin*, or a combination thereof. The application of the limonoid containing composition is preferably topical. In addition, the composition is preferably applied via a directed mode of delivery, for example, by topical application of an aqueous composition or transdermal patch.

In yet another embodiment, the present invention encompasses a method of treating hyperhidrosis or perspiration, comprising applying to skin a composition containing a limonoid in a cosmetically and/or dermatologically acceptable medium, and in an amount effective to treat, reduce, prevent and/or ameliorate hyperhidrosis or perspiration. In the method the limonoid is preferably a member of the family Maliaecae, more preferably the limonoid is a plant alkaloid, most preferably *toosendanin, azadirachtin*, or a combination thereof. The application of the limonoid containing composition is preferably topical.

Another embodiment of the present invention relates to a method of improving the aesthetic appearance of skin and comprises applying to the skin, or introducing via a directed mode of delivery, a composition including one or more limonoid constituents in an amount effective to improve the aesthetic appearance of the skin. According to this embodiment, the improvement in aesthetic appearance involves the treatment of at least one condition, such as signs of dermatological aging. Dermatological aging can include chronological aging, actinic aging, hormonal aging, or any combination thereof.

As will be appreciated by the practitioner, cosmetic treatments comprising compositions containing the limonoid constituents of the invention can be carried out, for example, by topically applying the cosmetic composition as described herein according to the routine technique for administering such compositions. Routine and commonly practiced techniques encompass the application of creams, lotions, gels, sera, ointments, antiperspirants, or deodorants to the skin; spraying as a form of application is also envisioned.

EXAMPLES

The following examples describe specific aspects of the invention to illustrate the invention and provide a description of the present methods for those of skill in the art. The examples should not be construed as limiting the invention, as the examples merely provide specific methodology useful in the understanding and practice of the invention and its various aspects.

Example 1

The plant alkaloids of the present invention can be extracted from natural raw materials by using the methods of organic solvent extraction or aqueous-organic solvent extraction, such as described in U.S. Pat. No. 6,372,239 to Wu et al., the contents of which are hereby incorporated by reference in their entirety and as set forth below.

Seed cell culture: Plant seed cells are extracted principally from the tissue of the embryo. The seed cell is then cultured. The total seed cell is then broken down through breaking or fracturing of cell walls to deliver the broad range of the plant cell constituents. Seed cell cultures are further disclosed in commonly owned patent application U.S. Ser. No. 10/040,242, which is hereby incorporated by reference herein in its entirety.

Organic solvent extraction The organic extraction method involves a step of continuous washing and extracting the plant material against a stream of organic solvent. Examples of organic solvents include, but are not limited to methanol, ethanol, dichloromethane, chloroform, xylene, and petroleum ether. For example, organic solvent extraction can be conducted in an extracting machine. Raw materials collected from the plant which contains the desired alkaloid(s), such as leaves, bark, seeds, fruits, and/or roots, are first ground to small particle sizes, and then put into the extracting machine through an inlet for the raw materials by a measurable charging machine. The plant materials are pushed by a thruster in the extracting machine and move forward slowly. Organic solvent (e.g., ethanol) is added into the machine through a solvent inlet at the top of a waste discharging outlet. Due to the difference of gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains low-concentration of extracted alkaloid(s). As a result of equilibrium, high yield of plant alkaloid(s) can be achieved by continuously extracting the plant material against the low-concentration solution.

The time of extraction is preferably between about 1–8 hours, more preferably between about 2–6 hours, and most preferably between about 3–5 hours. The temperature of extraction is preferably between about 30–90° C., more preferably between about 40–70° C., and most preferably between about 50–60° C. The collected extract is then fine-filtered to remove debris, and concentrated by distilling the solvent until the solid content reaches between about 25% and 45%. The distilled solvent can be reused for extraction.

Aqueous-organic solvent extraction Raw materials collected from a plant which contains the desired alkaloid(s), such as leaves, bark, seeds, and/or roots of the plant, are first ground to small particle sizes. The ground plant material is soaked in aqueous solution that is acidic or alkaline, depending on the solubility and stability of the desire alkaloid(s) under acidic or alkaline (basic) conditions. For extraction under acidic conditions, an acid such as hydrochloric acid or sulfuric acid is added to water at concentration of about 3% (w/v). For extraction under alkaline conditions, an alkali such as sodium hydroxide or sodium carbonate is added to water.

The time of extraction is preferably between about 1–8 hours, more preferably between about 2–6 hours, and most preferably between about 3–5 hours. The temperature of extraction is preferably between about 30–90° C., more preferably between about 40–70° C., and most preferably between about 50–60° C. The extract is then collected and fine-filtered to remove debris. Alkaline agents (e.g., ammonia) or acidifying agents (e.g., sulfuric acid) can be added to the extract to neutralize the solution by adjusting the pH, depending on the acidity or alkalinity of the collected extract. Organic solvent is then added to the neutralized solution to extract the alkaloid from aqueous phase to organic phase. Examples of such organic solvents include, but are not limited to, butanol, pentanol, hexanol and xylene. The extracted alkaloid(s) dissolved in organic solvent is/are concentrated until the solid content reaches about 50–80%.

It should be noted that different plants containing different kinds of alkaloids can be mixed and extracted together. This process of mixed extraction can preferably be used for extracting those plants containing alkaloids with similar solubility in the solvent used for extraction, such as ethanol. The mixture of alkaloids extracted can be concentrated and stored in an appropriate solvent.

*Toosendanin* has a molecular weight of 574.60, is colorless crystal, dissolves in methanol, chloroform and petroleum ether, and has a melting point of 244–245° C. For the extraction of *toosendanin* from *Melia toosendan* Sieb. et Zucc., dried seeds from *Melia toosendan* Sieb. et Zucc. can be ground and extracted against methanol. After fine-filtration and concentration, the extract containing *toosendanin* is transferred into turpentine and stored in a cool, dark place. The content of *toosendanin* is typically on the order of 20% by this procedure.

Methods for extracting *azadirachtin* from plant materials, e.g., neem seeds, are described in H1, 541 to K. S. Holla., the contents of which are hereby incorporated by reference in their entirety.

Plant extracts for obtaining limonoids for use according to the present invention are commercially available. For example, Ku Lian Pi extract (containing *toosendanin*) is available from Premier Specialties Inc., Middlesex, N.J. Ku Lian Pi is the Chinese name of the bark and root cortex of *Melia toosendan* Sieb. et Zucc., or *M. azedarach L.*; this material can also be called Cortex Meliae. In addition, neem seed cell broth is available from Phyton, Inc. Ithaca, N.Y. Neem extract is available from Carlisle International Corp. NY.

Example 2

Clinical Evaluation of Cosmetics Containing Limonoids

The safety and efficacy of a topically administered composition containing one or more limonoid constituents, e.g., *toosendanin* or *azadirachtin*, is studied in human subjects after a single-dose administration of a cosmetic formulation comprising the composition. Ten to fifteen panelists (preferably between 35 and 50 years old) with mild to moderate forehead lines and wrinkles are selected. The test subjects initially have a skin replicate made to establish a baseline depth and severity of wrinkles.

Dermatological tests are known in the art for testing the efficacy of an anti-wrinkling composition. Any such test would be useful for the present invention. For example, a layer of a flexible "non-cured" material, such as latex, may be applied to the skin. Upon removal of the "cured" material from the skin, the side that was adjacent to the skin can be assessed, either visually or via instrumentation, to determine the extent of wrinkling before treatment. The same area of skin may then be assessed after treatment to determine if there has been a change in number or depth of wrinkles.

On the following day, study technicians apply 0.6 grams of product (at a concentration of limonoid constituent of 140 mg/g) over an approximate 6 $cm^2$ semi-occlusive patch area on the subjects' foreheads. The product formulation preferably consists of a formulation designed to increase the penetration of water-soluble materials. The product remains on the subjects' skin for one hour. After the one hour exposure, a repeat skin replicate is taken to assess changes from the previous day. In addition, the subjects are asked to actively contract the forehead skin and brow to determine the overall efficacy and potency of the formulation.

Example 3

A composition comprising limonoid constituents according to the present invention is prepared to assess its effects on one or more dermatological related skin conditions. The composition is in the form of an oil-and-water emulsion and comprises the following ingredients:

TABLE 1

| Oil-in-Water Emulsion | |
|---|---|
| Ingredient | Amount |
| Humectant (e.g., glycols, glycerols) | 0.5–15% |
| Thickeners (e.g. gums, starches, polymers) | 0.1–4% |
| Chelants I (e.g. disodium EDTA; tetrasodium EDTA) | 0.001–0.5% |
| Preservatives | 0.01–2% |
| Sunscreen (e.g., benzophenone, ethylhexylmethoxycinnamate) | 0.1–50% |
| Silicone | 0.1–15% |
| Silica | 0.01–10% |
| Fatty Alcohol/Emulsifers/Wax/Fatty Acid | 0.5–15% |
| Emollients | 0.1–20% |
| Extracts for limonoid constituents (e.g., one or more of Neem seed cell broth, Ku Lian Pi extract, Neem extract or any combination) | 0.0001–50% |
| Demineralized water | Q.S. |

Example 4

A composition comprising limonoid constituents according to the present invention is prepared to assess its effects on one or more dermatological related skin conditions. The composition is in the form of an oil-and-water emulsion and comprises the following ingredients:

TABLE 2

| Oil-in-Water Emulsion | |
|---|---|
| Ingredient | Amount |
| Humectant (e.g., glycols, glycerols) | 0.5–15% |
| Thickeners (e.g. gums, starches, polymers) | 0.1–4% |
| Chelants I (e.g. disodium EDTA; tetrasodium EDTA) | 0.001–0.5% |
| Preservatives | 0.01–2% |
| Sunscreen (e.g. Parsol 1789; ethylhexylmethoxycinnamate; benzophenone-3) | 0.1–50% |
| Silicone | 0.1–15% |
| Silica | 0.01–10% |
| Fatty Alcohol/Emulsifers/Wax/Fatty Acid (e.g., ceteth-20 phosphate/cetearyl alcohol/dicetyl phosphate, Tribehenin PEG-20 Ester, Sodium Dihydroxycethyl | 0.5–15% |

TABLE 2-continued

Oil-in-Water Emulsion

| Ingredient | Amount |
|---|---|
| phosphate, cetearyl glucoside, cocoglyceride | |
| Emulsion Stabilizers/Viscosity Modifiers (e.g., acrylates/$C_{10-30}$ alkyl acrylate crosspolymer, Acrylate/Aminoacrylates/$C_{10-30}$ alkyl PEG-20 Itaconate, Sodium Acrylate/Acryloyldimethyl Taurate Coploymer, Acrylates/$C_{10-30}$ alkyl acrylate crosspolymer) | 0.1–20% |
| Film Formers (e.g. decene/butene copolymer, acrylates/octylacrylamide copolymer, adipic acid/diethylene glycol/glycerin crosspolymer | 0.001–2% |
| Emollients | 0.1–20% |
| Neem seed cell broth | 0.01–10% |
| Neem extract | 0.01–10% |
| Ku Lian Pi extract | 0.01–10% |
| Demineralized water | Q.S. |

Example 5

A composition comprising limonoid constituents according to the present invention is prepared to assess its effects on one or more dermatological related skin conditions. The composition is in the form of a water/silicone emulsion and comprises the following ingredients:

TABLE 3

Water/Silicone Emulsion

| Ingredient | Amount |
|---|---|
| Sodium PCA 50% | 0.1–4% |
| Sodium Lactate 60% | 0.01–10% |
| Sodium Chloride | 0.1–10% |
| Humectant (e.g., glycerin, glycols, glycerols) | 0.5–10% |
| Ammonium hydroxide | 0.01–10% |
| Cyclomethicon | 0.1–20% |
| Cyclomethicone/Dimethicone Copolyol | 0.1–20% |
| Emollients (e.g., cetyl octanoate) | 0.1–20% |
| Dimethicone Copolyol/Cyclopentasiloxane | 0.1–10% |
| Neem seed cell broth | 0.01–10% |
| Neem extract | 0.01–10% |
| Ku Lian Pi extract | 0.01–10% |
| Demineralized water | Q.S. |

Example 6

A composition comprising limonoid constituents according to the present invention is prepared to assess its effects on one or more dermatological related skin conditions. The composition is in the form of a gel and comprises the following ingredients:

TABLE 4

Gel

| Ingredient | Amount |
|---|---|
| Carbopol | 0.01–3% |
| Glycerin | 0.1–30% |
| Butylene glycol | 0.1–30% |

TABLE 4-continued

Gel

| Ingredient | Amount |
|---|---|
| Disodium EDTA | 0.01–2% |
| Methylparaben | 0.01–2% |
| Hydroxyethyl cellulose | 0.01–2% |
| Corn (*Zea mays*) starch | 0.01–10% |
| C.S. D&C Yellow No. 10 | 0.001–1% |
| C.S. FD&C Blue No. 1 | 0.001–1% |
| POE (20 M) methyl glucose ether | 0.01–10% |
| Dimethyl polysiloxane | 0.01–10% |
| PEG 50 Shea butter | 0.01–10% |
| Sodium hydroxide solution | 0.01–5% |
| Benzyl alcohol | 0.01–5% |
| Neem seed cell broth | 0.01–10% |
| Neem extract | 0.01–10% |
| Ku Lian Pi extract | 0.01–10% |
| Demineralized water | Q.S. |

Example 7

A composition comprising limonoid constituents according to the present invention is prepared to assess its effects on one or more dermatological related skin conditions. The composition is in the form of a cleansing foam and comprises the following ingredients:

TABLE 5

Cleansing Foam

| Ingredient | Amount |
|---|---|
| Humectant (e.g., glycerin, butylene glycol) | 5–25% |
| Polethylene glycol | 0.1–20% |
| Bentonite | 0.1–20% |
| Stearic acid | 0.1–30% |
| Myristic acid | 0.1–20% |
| Cetearyl Alcohol/Ceteareth-20 | 1.00000% |
| Potassium hydroxide 45% | 0.1–20% |
| Preservatives (e.g., Benzyl alcohol, 2-Phenoxyethanol) | 0.1–10% |
| Neem seed cell broth | 0.01–10% |
| Neem extract | 0.01–10% |
| Ku Lian Pi extract | 0.01–10% |
| Demineralized water | Q.S. |

Example 8

A liposome composition comprising limonoid constituents according to the present invention is prepared as follows:

TABLE 6

Liposome

| Ingredient | Amount |
|---|---|
| Lecithin | 5–25% |
| $C_{12-15}$ alkyl benzoate | 1–15% |
| Quaternium 15 | 0.01–2% |
| Parabens | 0.01–2% |
| Neem seed cell broth | 0.01–10% |
| Neem extract | 0.01–10% |
| Ku Lian Pi extract | 0.01–10% |

The contents of all patents, patent applications, published articles, abstracts, books, reference manuals and abstracts, as cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method for treating wrinkles and/or fine lines of the skin, comprising administering to a subject in need of treatment a composition comprising one or more limonoid constituents in an amount effective to ameliorate, reduce, and/or eliminate wrinkles and/or fine lines.

2. The method according to claim 1, wherein the composition is a topical composition.

3. The method according to claim 2, wherein said composition is applied for a period of time effective to ameliorate, reduce, and/or eliminate wrinkles and/or fine lines.

4. The method according to claim 1, wherein the one or more limonoid constituents is selected from *toosendanin, azadirachtin*, or a combination thereof.

5. The method according to claim 3, wherein the composition is applied once daily for at least one week.

6. The method according to claim 1, wherein the one or more limonoid constituent is present in an amount of from about 0.0001 wt % to about 10 wt % of the total weight of the composition.

7. The method according to claim 1, wherein the one or more limonoid constituent is present in an amount of from about 0.0005 wt % to about 5 wt % of the total weight of the composition.

8. The method according to claim 1, wherein the one or more limonoid constituent is present in an amount of from about 0.001 wt % to about 1 wt % of the total weight of the composition.

9. The method according to claim 1, wherein the composition comprises a cosmetically or dermatologically acceptable vehicle, carrier or diluent.

10. The method according to claim 1, wherein the composition further comprises a sunscreen.

11. The method according to claim 10, wherein the sunscreen is selected from the group consisting of avobenzone, cinnamic acid derivatives, octyl salicylate, oxybenzone, titanium oxide, zinc oxide and combinations thereof.

12. The method according to claim 11, wherein the cinnamic acid derivative is octylmethoxycinnamate.

13. The method according to claim 10, wherein the composition further includes an ingredient selected from the group consisting of an alpha hydroxy acid, an oxa acid and an oxa diacid.

14. The method according to claim 1, wherein the composition is administered via a transdermal patch.

15. The method according to claim 1, wherein the composition is subcutaneously or intradermally injected.

16. The method according to claim 1, wherein the composition is administered via iontophoresis.

17. The method according to claim 1, wherein the composition is applied to the face and the limonoid constituent inhibits acetylcholine release at a neuromuscular junction of a facial expression muscle, thereby relaxing muscle associated with marionette lines, wrinkles on the forehead, or wrinkles between the brows.

18. A method of improving the aesthetic appearance of skin, comprising topically applying to the skin a composition comprising one or more limonoid constituents in an amount effective to improve the aesthetic appearance of skin.

19. The method according to claim 18, wherein the improvement in aesthetic appearance is selected from the group consisting of makes facial lines appear less noticeable, makes facial lines and/or wrinkles feel plumped, improves appearance of suborbital lines and/or periorbital lines, improves appearance of crow's feet, reduces and/or diminishes the appearance of wrinkles, reduces and/or eliminates fine and/or deep lines, folds, furrows, and creases, smoothes skin, and combinations thereof.

20. The method according to claim 18, wherein the skin is sensitive skin.

21. The method according to claim 18, wherein the composition is applied topically at least once daily for at least one week.

22. The method according to claim 18, wherein the one or more limonoid constituents is present in an amount of from about 0.0001 wt % to about 10 wt % of the total weight of the composition.

23. The method according to claim 18, wherein the one or more limonoid constituents is present in an amount of from about 0.0005 wt % to about 5 wt % of the total weight of the composition.

24. The method according to claim 18, wherein the one or more limonoid constituents is present in an amount of from about 0.001 wt % to about 1 wt % of the total weight of the composition.

25. The method according to claim 18, wherein the composition comprises a cosmetically or dermatologically acceptable vehicle, carrier or diluent.

26. The method according to claim 18, wherein the composition is administered in a liposome delivery vehicle.

27. The method according to claim 26, wherein the composition in the liposome delivery vehicle is administered topically.

28. The method according to claim 18, wherein the composition is administered via a transdermal patch.

29. The method according to claim 18, wherein the composition is administered via ontophoresis.

30. The method according to claim 18, wherein the composition further comprises a sunscreen.

31. The method according to claim 30, wherein the sunscreen is selected from the group consisting of avobenzone, cinnamic acid derivatives, octyl salicylate, oxybenzone, titanium oxide, zinc oxide and combinations thereof.

32. The method according to claim 31, wherein the cinnamic acid derivative is octylmethoxycinnamate.

33. The method according to claim 30, wherein the composition further includes an ingredient selected from the group consisting of an alpha hydroxy acid, an oxa acid and an oxa diacid.

34. A method of treating, reducing, ameliorating, and/or eliminating, wrinkles, fine lines, or deep frown lines in the skin, comprising: providing a composition comprising acetylcholine release inhibitor to an individual in need thereof, in an amount effective to block or reduce acetylcholine release at a neuromuscular junction (NMJ), wherein said inhibition or reduction of acetylcholine release at the neuromuscular junction (NMJ) concomitantly inhibits or reduces contraction of muscle tissue, thereby treating, reducing, ameliorating, and/or eliminating wrinkling, fine lines, or deep frown lines in the skin.

35. The method according to claim 34, wherein the acetylcholine release inhibitor is one or more limonoid constituents.

36. The method according to claim 35, wherein the one or more limonoid constituents is selected from *toosendanin*, *azadirachtin*, or a combination thereof.

37. The method according to claim 34, wherein the composition is topically applied to the skin.

38. The method according to claim 34, wherein the composition is contained in a liposome delivery vehicle or a transdermal patch.

39. The method according to claim 34, wherein the composition further includes a sunscreen.

40. The method according to claim 39, wherein the sunscreen comprises one or more ingredients selected from the group consisting of avobenzone, cinnamic acid derivatives, octyl salicylate, oxybenzone, titanium oxide, zinc oxide, an alpha hydroxy acid, an oxa acid, an oxa diacid and mixtures or combinations thereof.

41. The method according to claim 35, wherein the one or more limonoid constituents is present in an amount of from about 0.0001 wt % to about 10 wt % of the total weight of the composition.

42. The method according to claim 35, wherein the one or more limonoid constituents is present in an amount of from about 0.0005 wt % to about 5 wt % of the total weight of the composition.

43. The method according to claim 35, wherein the one or more limonoid constituents is present in an amount of from about 0.001 wt % to about 1 wt % of the total weight of the composition.

* * * * *